United States Patent
Karlen et al.

(10) Patent No.: US 6,264,929 B1
(45) Date of Patent: Jul. 24, 2001

(54) HAIR TREATMENT COMPOSITIONS CONTAINING FLUORINATED ACIDS AND POLYMERS

(75) Inventors: Thomas Karlen, Bern; Daniel Chambettaz, Ursen, both of (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/244,941

(22) Filed: Feb. 4, 1999

(30) Foreign Application Priority Data

Feb. 11, 1998 (DE) ............................... 198 05 434

(51) Int. Cl.[7] ........................... A61K 47/06; A61K 7/075; A61K 7/00
(52) U.S. Cl. .................. 424/70.1; 424/70.22; 424/70.24; 424/400; 424/401
(58) Field of Search ................ 424/70.1, 70.22, 424/70.24, 400, 401

(56) References Cited

U.S. PATENT DOCUMENTS

| 3,993,744 | 11/1976 | Cella et al. ......................... 424/71 |
| 3,993,745 | 11/1976 | Cella et al. . |
| 4,066,589 | 1/1978 | Langford et al. ............... 260/29.6 H |
| 4,304,563 | 12/1981 | Grollier et al. . |
| 4,419,298 | * 12/1983 | Falk et al. ...................... 260/501.16 |
| 5,948,396 | 9/1999 | Das et al. . |
| 5,980,876 | 11/1999 | Peffly . |

FOREIGN PATENT DOCUMENTS

| 43 44 478 A1 | 6/1995 | (DE) . |
| 93/03703 | 3/1993 | (WO) . |
| 93/03704 | 3/1993 | (WO) . |
| WO 95/35087 | 12/1995 | (WO) . |

\* cited by examiner

*Primary Examiner*—Shelley A. Dodson
(74) *Attorney, Agent, or Firm*—Michael J. Striker

(57) ABSTRACT

Compositions for treating hair prepared using fluorinated acids to neutralize polymers with basic groups are described, which contain a complex formed from at least one fluorinated acid and at least one polymer with basic groups or a complex of a salt of a fluorinated acid and a polymer with protonated or quaternized amine groups, and which also contain at least one film-forming, hair-fixing polymer. These compositions deposit a reduced amount of residue on the hair without reducing the hair-fixing performance.

14 Claims, No Drawings

HAIR TREATMENT COMPOSITIONS CONTAINING FLUORINATED ACIDS AND POLYMERS

BACKGROUND OF THE INVENTION

FIELD OF THE INVENTION

The present invention concerns the use of fluorinated acids for neutralization of polymers with basic groups in hair treatment compositions. The subject matter of the invention also includes hair treatment compositions containing (A) a complex formed from at least one fluorinated acid and at least one polymer with basic groups or a complex of a salt of a fluorinated acid and a protonated polymer with protonated or quaternary amine groups and (B) at least one film-forming, hair-fixing polymer.

Hair styling products are those products, which provide the hair with hold, volume, elasticity, springiness and luster by means of polymer additives. In the first place they bring the hair into a shape (for example, gels), they impart stand to the hair (for example, hair sprays) or they give volume to the hair (for example, fixing foams).

That residue in the form of fine or gross flakes can be formed when the hair is pushed together by motions is a known problem with hair styling products. This occurs, e.g., when the hair is combed or brushed or also when the hair is contacted with materials, e.g. during motion of the head on a pillow. These residues are considered to be unaesthetic by consumers and make frequent hair washing necessary. Thus it is desirable to minimize the residue formation by hair styling products as much as possible without impairing the positive properties of these products.

It is known to improve the residue properties of hair fixing compositions by working materials, such as silicone oils, surfactant compounds, oils, or the like, into the formulation. The use of these materials has the disadvantage that the films formed have a reduced fixing effect. Either a comparatively larger amount of these compositions must be applied or the polymer content of these products must be increased in order to obtain a predetermined styling hold. These additive materials have the additional disadvantage that they load the hair and impart an oily fatty aspect to it.

SUMMARY OF THE INVENTION

It is an object of the present invention to provide an improved hair treatment composition, especially a hair fixing composition, which has good residue properties without the above-described disadvantages.

It has been found that the use of fluorinated acids in styling products, which contain at least one polymer with basic groups, provides an improvement in the residue properties of the composition, without degrading the fixing or causing loading of the hair.

The subject matter of the invention includes the use of fluorinated acids for neutralization of polymers with basic groups in compositions for treatment of the hair, especially in hair fixing compositions. Homopolymers or copolymers, which are formed from at least one type of monomer, which contains a basic group, especially a basic nitrogen atom, are the polymers with basic groups in the sense or meaning of the invention. Preferably these polymers contain no acidic or anionic groups and also have no amphoteric character, but only contain the basic groups.

The hair treatment composition according to the invention contains a complex formed from at least one fluorinated acid and at least one polymer with a primary or secondary amino group or a complex of a salt of a fluorinated acid and a protonated polymer with protonated primary or secondary amine groups. Polymers with primary or secondary amino groups in the sense of the invention are homopolymers or copolymers that are built up from at least one type of monomer, which contains a primary or secondary amino group. Also in these polymers it is a matter preferably of polymers which contain no acidic or anionic groups and also have no amphoteric character, but only contain basic groups.

The subject matter of the invention also includes a hair treatment composition with a content of (A) a complex formed from at least one fluorinated acid and at least one polymer with basic groups or a complex of a fluorinated acid salt and a protonated polymer with protonated or quaternary amino groups, in which the protonated polymer is preferably free of acid or anionic groups, and (B) at least one film-forming, hair-fixing polymer.

The film-forming hair-fixing polymer (B) preferably is contained in the hair treatment composition of the invention preferably in an amount of from 0.01 to 50 percent by weight, especially preferably in an amount of from 0.5 to 50 percent by weight.

By the term "complex" in the sense of the present invention an ion pair is understood which is formed from at least one anion of a fluorinated acid and a polymer with cationic groups.

The fluorinated acids or their salts are preferably present in an amount of from 0.01 to 10 percent by weight, especially preferably of from 0.05 to 5 percent by weight. The polymer with basic groups or the protonated polymer with protonated amine groups is preferably present in an amount of from 0.01 to 20 percent by weight. An aqueous or aqueous-alcoholic solvent system is preferred.

The fluorinated acid is preferably a compound having the general formula (I):

$$A-(CH_2)_x-(CF_2)_y-(CH_2)_z-B \qquad (I),$$

in which x and z, independently of each other, are each a number from 0 to 5, y is a number from 1 to 21, A is an acid group and B is either a fluorine atom or an acid group, with the proviso that z has the value 0 when B represents a fluorine atom. The acid groups A and B are preferably selected from the group consisting of —COOH, —SO$_3$H, —OPO$_3$H$_2$ and —OPO$_2$H.

Suitable fluorinated acids are, especially, perfluorinated acids, such as trifluoromethanesulfonic acid, perfluoropropionic acid, trifluorobutyric acid, perfluoropentanoic acid, perfluorohexanoic acid, perfluoroheptanoic acid, perfluorooctanoic acid, perfluorononanoic acid, perfluorodecanoic acid, perfluorododecanoic acid, perfluoroglutaric acid, perfluorosebacic acid, perfluorooctanesulfonic acid, mixtures of perfluorinated phosphinic/phosphonic acids marketed by Clariant (Germany) under the trade name Fluowet® PL 80 and perfluorooctanoic acid marketed by 3M under the trade name Fluorad® FX 1001.

Other suitable fluorinated acids include partially fluorinated acids, such as 3H-decafluorohexanoic acids, 6-fluorohexanoic acid, 4,4,5,5,6,6,6-heptafluorohexanoic acid, 5,5,5-trifluorovaleric acid, 2H,2H-heptafluorovaleric acid, 5H-ocotafluorovaleric acid, 3H-octafluorovaleric acid and 2H-decafluoropentan-1-sulfonic acid.

Those compounds according to formula (I) which are soluble in aqueous or in aqueous/alcoholic solution with a water content of at least 10% are preferred. Those compounds according to formula (I) which are solution in purely aqueous solutions, such as perfluoropentanoic acid, perfluorobutyric acid, perfluoropropionic acid or perfluoroglutaric acid, are especially preferred.

The polymers with basic groups having a molecular weight of preferably at least 50,000 g/mol, especially preferably from 100,000 to 6,000,000 g/mol and contain nitrogen-containing groups, such as primary, secondary or tertiary amines. The advantage of the polymers with primary or secondary amine groups is the great affinity of the fluorinated acids for these groups. The resulting complex between the polymers and fluorinated acids is stabilized because the fluorine groups remain in the polymer film and do not migrate from it.

The basic groups are either located in the polymer chain or preferably are substituents in one or more monomers. The polymer with the basic groups can be natural or synthetic homo- or copolymers with amine substituted monomers units and, if necessary, with non-basic comonomers. Suitable polymers with basic groups are, for example, copolymers of amine-substituted vinyl monomers and non-amine substituted monomers. Amine substituted vinyl monomers include,, for example, dialkylaminoalkyl acrylates, dialkylaminoalkylmethacrylate, monoalkylaminoalkylacrylates and monoalkylaminoalkylmethacrylates, wherein the alkyl groups of these monomers are preferably lower alkyl groups, such as $C_1$- to $C_7$-alkyl groups, especially preferably $C_1$- to $C_3$-alkyl groups.

Non-amine substituted comonomers for use in the compositions of the invention include, for example, acryl amide, methacrylamide, alkyl- and dialkylacrylamide, alkyl- and dialkylmethacrylacide, alkylacrylate, alkylmethacrylate, vinylcaprolactone, vinylpyrrolidone, vinyl ester, vinyl alcohol, maleic acid anhydride, propylene glycol and ethylene glycol. The alkyl groups of these monomers are preferably $C_1$- to $C_7$-alkyl groups, especially preferably $C_1$- to $C_3$-alkyl groups.

One preferred polymer with basic groups consists of chitosan or a chitosan derivative compound, especially chitosan having a molecular weight of from 20,000 to about 5,000,000 g/mol. For example a low molecular weight chitosan with a molecular weight of from 30,000 to 70,000 g/mol or a high molecular weight chitosan with a molecular weight of from 300,000 to 700,000 g/mol. The preferred deacylation degree for the chitosan is between 10 and 99 percent. The neutralization degree for chitosan or for the chitosan derivative compounds is preferably at least 50%, especially preferably between 70 and 100%, in relation to the number of free basic groups.

Additional preferred polymers with basic groups include amphoteric polymers, such as copolymers formed from alkylacrylamides, especially octylacrylamide, alkylaminoalkylmethacrylates, especially t-butylaminoethylmethacrylates, and two or more monomers comprising acrylic acid, methacrylic acid or their esters, such as those marketed under the trade name Resyn 28-4910, Amphomer or Amphomer LV-71 of National Starch, USA.

The basic groups of the polymer are partially or completely neutralized with fluorinated acids in the compositions according to the invention. However those compositions of the invention in which the basic groups of the polymer are neutralized from 5 to 70% with the fluorinated acids preferably are neutralized by additional non-fluorinated neutralizing agents, which are commonly used in hair cosmetic arts. Organic or inorganic acids can be used as the additional neutralizing agents. For example, acids of this type are formic acid, tartaric acid, malic acid, lactic acid, citric acid, pyrrolidone carboxylic acid and hydrochloric acid, among others.

If the polymer with basic groups also has acid-containing groups, such as can be the case with amphoteric polymers, the acid groups can be neutralized with a base, before the basic groups are neutralized with the fluorinated acids. For example, suitable bases for this purpose include aminomethylpropanol, triethanolamine, monoethanolamine and sodium hydroxide, among others.

The polymers with the basic groups can be water-soluble or water-insoluble. However preferably the polymers, which are water-insoluble when basic groups in unneutralized form are present are water-soluble after partial or complete neutralization with fluorinated acids.

The polymers with basic groups can be substantive or non-substantive for keratinic material. Polymers are preferred, which are non-substantive after neutralization. The term "non-substantive" means generally those polymers which can be removed by a single washing of the hair or are already removed by a single rinsing of the hair with water.

The polymers with quaternary amine groups, which are used in the composition according to the invention in combination with salts of fluorinated acids and at least one film-forming hair-fixing polymer, can be homo- or copolymers, in which the quaternary amine groups are either found in the polymer backbone or preferably as substituents in one or more of the monomers. The ammonium groups containing the monomers can be copolymerized with the above-described non-amine substituted monomers. Suitable ammonium substituted vinyl monomers are, for example, trialkylmethacrylicoxyalkylammonium vinyl monomers, tiralkylacryloxyalkylammonium vinyl monomers, dialkyldiallylammonium vinyl monomers and quaternary vinyl ammonium monomers with cyclic, cationic nitrogen containing groups such as pyridinium, imidazloium or quaternary pyrrolidone, e.g. alkylvinylimidazolium salts, alkylvinylpyridinium dalts or alkylvinylpyrrolidone salts. The alkyl groups of these monomers are preferably lower alkyl groups, for example $C_1$- to $C_7$-alkyl groups, especially preferably $C_1$- to $C_3$-alkyl groups.

Suitable polymers with quaternary amine groups are, for example, the polymers described in CTFA Cosmetic Ingredient Dictionary under the tradename, Polyquaternium, such as methylvinylimidazolium chloride/vinyl pyrrolidone copolymer (Polyquaternium-16), quaternized vinyl pyrrolidone/dimethylaminoethylmethacrylate copolymer (polyquaternium-11), homo- and copolymers of dimethyldiallyammonium chloride (Poly-quaternium-6 and -7), quaternarized hydroxyethylcellulose (Polyquaternium-10) or quaternized guar derivative compounds.

The film-forming and hair-fixing polymers of ingredient (B) can be synthetic or natural, non-ionic, cationic, anionic or amphoteric polymers. The hair-fixing polymers can be used individually or in a mixture. The term "film-forming, hair-fixing polymers" means those polymers which, when used alone in a 0.1 to 5% aqueous alcoholic or aqueous-alcoholic solution, are in a position to deposit a polymer film on the hair and in this way to fix the hair.

Suitable synthetic, nonionic, film-forming hair-fixing polymers are, for example, homopolymers of vinylpyrrolidones, which, e.g. are sold under the trade name LUVISKOL®K of BASF, Germany, or PVP-K of ISP, USA, and homopolymers of N-vinylformamide, which, e.g., is sold under the trade name PVF of National Starch, USA. Additional suitable synthetic film-forming non-ionic hair-fixing polymers are, e.g., copolymerizates of vinyl pyrrolidone and vinyl acetate, which, for example, are sold under the trade name LUVISKOL® VA of BASF, Germany; terpolymers of vinylpyrrolidone, vinylacetate and vinylpropionate, which are sold under the trade name LUVISKOL®VAP of BASF, Germany; polyacrylamides, which are sold under the trade name AKYPOMINE® P 191 of CHEM-Y, Germany or SEPIGEL®305 of SEPPIC, USA; polyvinyl alcohols, which are sold, e.g., under the trade name ELVANOL® of DuPont or VINOL® 523/540 of Air Products, USA; and high molecular polyethylene glycols or high molecular weight copolymers of ethylene glycol with propylene glycol with fixing properties, which, for example, are marketed under the trade name LIPOXOL® 1000 of H ÜLS AG, Germany, PLURACOL E 4000 of BASF, Germany, or UPIWAX® 20,000 of UPI.

Suitable synthetic film-forming anionic polymers are, for example, cross-linked or non-cross-linked vinyl acetate/ crotonic acid copolymers, which for example are sold in the form of a 60% solution of isopropanol/water under the trade name ARISTOFLEX® of HOECHST, Germany, or by BASF under the trade name LUVISET CA-66. Additional suitable anionic polymers are, for example, terpolymers of acrylic acid, alkyl acrylate and N-alkylacrylamide, especially acrylic acid/ethylacrylate/N-t-butylacrylamide terpolymers, such as those marketed under the tradename ULTRAHOLD 8 and ULTRAHOLD STRONG of BASF, Germany, or terpolymers made from vinylacetate, crotonate and vinylalkanoate, especially vinylacetate/crotonate/ vinylneodecanoate copolymers, such as those that are marketed, for example, by National Starch under the tradename RESYN 28-2930.

Suitable natural film-forming polymers with hair fixing action include, for example, different kinds of saccharides, for example polysaccharides or mixtures of oligo-, mono- and disaccharides, which, for example, are sold under the trade name C-PUR® of Cerestar, Brussels, Belgium. Additional suitable natural polymers include Chinese Balsamic resin and cellulose derivative compounds, for example hydroxypropyl cellulose having a molecular weight of 30,000 to 50,000 g/mol, which for example are sold under the trade name NISSO SL® of Lehmann & Voss, Germany. An additional natural polymer is shellac. Shellac can be used in neutralized or unneutralized form.

Cationic polymers, which can be included in the compositions of the invention, include for example polyvinylpyrrolidone/dimethylaminoethylmethacrylate copolymers, which are sold under the trade name Gafquat® 755 N of GAF Co, USA. Additional cationic polymers include, e.g., the copolymers of polyvinylpyrrolidone and imidazoliminemethochloride sold for example by BASF AG, Germany, under the trade name LUVIQUAT® HM 550; the terpolymer of dimethyldiallylammonium chloride, sodium acrylate and acrylamide sold under the trade name MERQUAT® Plus 3300 by Calgon, USA; the terpolymer of vinylpyrrolidone, dimethylaminoethylmethacrylate and vinylcaprolactam sold by ISP, USA, under the trade name Gaffix® VC 713; the quaternary ammonium salt of hydroxyethyl cellulose and a trimethylammonium-substituted epoxide marketed under the trade name Polymer IR® by Amerchol, USA; the vinylpyrrolidone/ methacrylamidopropyltrimethylammonium chloride copolymer sold under the trade name GAFQUAT® HS 100 by GAF and the diquaternary polydimethylsiloxane sold under the trade name Abil® Quat 3272 by Goldschmidt, Germany.

Furthermore polymers with thickening action can also be used in the compositions according to the invention.

Thickener compounds, which can be included in the compositions of the invention, include homopolymers of acrylic acid with a molecular weight of 2,000,000 to 6,000,000, which for example are marketed by BF Goodrich, USA, under the trade name Carbopol®. Additional thickeners which can be included in the compositions of the invention include acrylic acid homopolymers with a molecular weight of 4,000,000 or about 4,000,000, which are marketed under the trade name Carbopol® 940 by BF Goodrich. Other thickeners include acrylic acid homopolymers sold by BF Goodrich under the trade name Carbopol® ETD 2001 or by Protex, France, under the tradename Modarez V 600 PX; polymers made from acrylic acid and acryl amide (sodium salt) with a molecular weight of 2,000,000 to 6,000,000 marketed under the trade name Hostacerin® PN 73 by Hoechst, Germany; and sclerotium gum sold by the Alban Mueller Company, Montreuil, France, under the trade name Amigel®. Copolymers of acrylic acid or methacrylic acid, such those sold under the tradename Carbopol 1342 or Pemulen TR1 of Goodrich, USA, are particularly preferred in the compositions of the invention.

The composition according to the invention is preferably provided in an aqueous or an aqueous-alcoholic medium. Solvents or mixtures of solvents with a boiling point under 400° C. are used in the compositions of the invention in amounts of from 0.1 to 90 percent by weight, preferably from 1 to 50 percent by weight. Branched or nonbranched hydrocarbons, such as pentane, hexane and isopentane, and cyclic hydrocarbons, such a cyclopentane and cyclohexane, are preferred as solvents for the compositions of the invention. Lower alcohols with 1 to 4 carbon atoms suitable for cosmetic purposes, such as ethanol and isopropanol, can be contained in the compositions of the invention as solvents. Glycerol and propylene glycol in amounts up to 30 percent by weight are especially preferred as water-soluble solvents for the compositions of the invention.

Understandably the composition of the invention can also contain additional conventional cosmetic additives, such as non-fixing, nonionic polymers, for example polyethylene glycols or copolymers of ethylene glycol and propylene glycol, non-fixing anionic polymers and nonfixing natural polymers and their combinations in an amount of preferably 0.01 to 50 percent by weight; perfume oils in amounts of preferably 0.01 to 5 percent by weight; turbidity-inducing agents, such as ethylene glycol distearate, in an amount of preferably 0.10 to 5 percent by weight; wetting agents or emulsifiers from the classes of anionic, cationic, amphoteric or nonionic surface-active substances without washing action, such as fatty alcohol sulfates, ethoxylated fatty alcohols, fatty acid alkanol amides, such as esters of hydrogenated castor oil fatty acids, in an amount of preferably from 0.01 to 30 percent by weight; moisture-containing agents, dye compounds, light protective agents, antioxidants, luster-imparting agents and preservatives in an amount of preferably 0.01 to 10 percent by weight.

Suitable silicone polymers can also be used as additives in the composition of the invention, for example polydimethylsiloxane (INCI: dimethicone), α-hydro-ω-hydroxypolyoxydimethylsilylene (INCI: dimethiconol), cyclic dimethylpolysiloxane (INCI: cyclomethicone), trimethyl-(octadecyloxy)silane (INCI: stearoxytrimethylsilane), dimethylsiloxane-glycol copolymer (INCI: dimethicone copolyol), dimethylsiloxaneaminoalkylsiloxane copolymer with hydroxy end groups (INCI: amodimethicone), monomethylpolysiloxane with lauryl side chains and polyoxyethylene and/or polyoxypropylene chains (INCI: lauryl methicone copolyol), dimethylsiloxane glycol copolymer acetate (INCI: dimethicone copolyol acetate), dimethylsiloxane-aminoalkylsiloxane copolymer with trimethylsilyl end groups (INCI: trimethylsilylamodimethicone). Preferred silicone polymers are: dimethicone, which for example is marketed by Wacker, Munich, Germany, under the trade name SILOXANE F-221 or under the trade name DOW CORNING FLUID 200/0.65 Cs by Dow Corning Europe, Brussels, Belgium; cyclomethicone, which for example is sold under the trade name DOW CORNING 244 Fluid by Dow Corning Europe, Brussels, Belgium, or under the trade name ABIL® K4 of Goldschmidt, Germany; dimethiconol, which was sold under the trade name SILICONE FLUID F-212 of Wacker, Germany, or UNISIL® SF-R of UPI.

The designations for the compounds in parentheses above are in accordance with INCI (International Cosmetic Ingredients) nomenclature for cosmetic active and auxiliary substances.

Mixtures of silicone polymers are also suitable, for example, a mixture of dimethicone and dimethiconol, which for example is sold under the trade name DOW CORNING 1403 Fluid of Dow Corning, Europe, Belgium.

An additional advantage of the present invention is that fluorinated acids, especially perfluorinated acids, are in a position to stablize chitosan in aqueous aerosol spray formulations, e.g. hair sprays, which have a reducing content of volatile organic ingredients (VOC).

For the foregoing reason the present invention also includes a aerosol spray containing:

(A) chitosan or a basic chitosan derivative compound, (B) at least one fluorinated acids, (C) water in an amount of preferably at least 10 percent by weight, especially preferably at least 30 percent by weight, and (D) at least one turbidity-inducing agent, The hair sprays of the invention contain at maximum 80 percent by weight VOC, but preferably up to a maximum of 55 percent by weight VOC.

The compositions according to the invention can be used in different forms for various applications, such as in aerosol preparations, for example foams or sprays or non-aerosol forms which are applied by means of a pump or used as a "pump and spray" composition. The compositions according to the invention may also be used in the form of conventional O/W and W/O emulsions, gels, waxes or microemulsions. The compositions according to the invention can also be formulated as hair dye compositions or hair care compositions, for example a dye-fixing and hair rinsing compositions.

When the compositions according to the invention are in the form of an aerosol hair spray or aerosol hair lacquer, they contain 15 to 85 percent by weight, preferably 25 to 75 percent by weight of a propellant and are filled in a pressurized container. Lower alkanes, such as n-butane, i-butane and propane, or their mixtures with dimethyl ether, as well as gaseous propellants, such as $N_2$, $N_2O$ and $CO_2$, providing the pressures occurring in the pressurized container, are suitable as the propellant.

The compositions according to the invention for fixing hair can also be in the form of a non-aerosol hair spray or a non-aerosol hair lacquer that is sprayed mechanically with the help of a suitable mechanical spraying apparatus. The term "mechanical spraying apparatus" means an apparatus that facilitates the spraying of a liquid without use of a propellant. A spray pump or an elastic container provided with a spray valve can be used as a suitable mechanical spraying apparatus. The elastic container is filled with the cosmetic composition according to the invention under pressure, which expands the elastic container so that the composition is dispensed from it because of its contraction when the spray valve is opened.

Furthermore the polymer combination according to the invention permits the making of concentrates with reduced water or solvent content. The concentrates are converted into the hair treatment compositions according to the invention by addition of the required amount or water or solvent after being transported and, if necessary, stored.

The term "hair treatment" means the treatment of human head hair and above all for the purpose of hair styling or care of the hair.

The compositions according to the invention have improved residue properties, without loss of fixing performance. The resistance of the polymer films to moisture-take-up is increased, whereby an improved fixing hold is attained at a high humidity.

The following examples illustrate the subject matter of the invention, the details of which should not be considered as further limiting the general concept of the invention expressed in the claims appended hereinbelow.

EXAMPLES

Example 1

The following compositions were prepared including composition no. 1, which was not of the invention, and composition no. 2, which is a composition of the invention:

| Ingredient | Composition No.1, Not of the invention | Composition No. 2, of the Invention |
|---|---|---|
| Chitosan | 0.80 g | 0.80 g |
| Perfluoropentanoic acid | — | 0.23 g |
| Formic acid, 85% | 0.24 g | 0.19 g |
| PVP/VA copolymer | 1.00 g | 1.00 g |
| PVP polymer | 1.00 g | 1.00 g |
| Polyquaternium 16 | 0.50 g | 0.50 g |
| Cetyltrimethyl-Ammonium chloride | 0.10 g | 0.10 g |
| Ethanol, 94.7% | 10.00 g | 10.00 g |
| Water | 86.36 g | 86.18 g |
| Total | 100.00 g | 100.00 g |

*Polyquaternium-16: methylvinylimidazolium chloride/vinyl-pyrrolidone copolymer.

The effective action of the foam-fixing solution no. 1 was compared in regard to residue formation and hair fixing performance with that of the effective substance-containing solution no. 2 according to the invention.

Residue Formation:

Five hair tresses were each treated with an equal weight and to an equal extent with the same amount of foam-fixing solutions no. 1 and no. 2 and were dried at 20° C. at a predetermined humidity. The amount of the residue was measured with the help of the following methods of analysis.

After passing a comb once through each hair strand the whiteness proportion of 10 non-overlapping square regions on a 1-cm×1-cm surface was measured. The measurement produced the following residue results for both compositions (% whiteness of the entire surface). The residue result for each composition was an average value obtained from values measured in the 10 square regions for the 5 hair strands and thus was the result of averaging a total of fifty values:

2.69+/−0.26 No. 1

2.04+/−0.28.

Thus composition no. 2 of the invention containing the perfluoropentanoic acid provides 24% less residue than composition no. 1 which is not of the invention because it does not contain that ingredient. From these results already a definite conclusion can be drawn, namely that the residue on the hair can be reduced by neutralization of the chitosan present with perfluoropentanoic acid.

Fixing Action:

The fixing strengths of the foam-fixing solutions no. 1, not of the invention, and no. 2, of the invention, were measured with the help of a breaking force measurement of the hair strands (9 measurements per effective solution, the results given in Newtons).

0.123+/−0.029                No. 1

0.131+/−0.025                No. 2

These measurements show that there is no significant difference between the fixing performance of these two solutions.

Thus these comparative experimental results for residue formation and breaking strength show that the use of perfluorinated acids in hair fixing composition no. 2 reduces residue formation while maintaining fixing performance.

Example 2

Foam-fixing Composition

| | |
|---|---|
| 1.00 g | polyvinylpyrrolidone |
| 1.00 g | PVP/vinyl acetate copolymer |
| 1.00 g | chitosan |
| 0.24 g | formic acid, 85% |
| 0.29 g | perfluoropentanoic acid |
| 0.20 g | cetyltrimethyl ammonium chloride |
| 1.00 g | polyquaternium 16 |
| 10.00 g | ethanol |
| 85.27 g | water |
| 100.00 g | |

The filling occurs with 92% active substance solution and 8% propane/butane. The foam produces a good, flexible fixing and may be removed again by brushing out, without loading the hair.

Example 3

Foam-fixing Composition With Strong Fixing Action

| | |
|---|---|
| 0.50 g | polyvinylpyrrolidone |
| 0.50 g | PVP/vinyl acetate copolymer |
| 0.50 g | high molecular weight, chitosan, 300,000 to 700,000 g/mol |
| 0.35 g | pyrrolidone carboxylic acid |
| 0.17 g | pentafluoropropanoic acid |
| 0.20 g | cetyltrimethyl ammonium chloride |
| 1.00 g | polyquaternium 16 |
| 10.00 g | ethanol |
| 86.78 g | water |
| 100.00 g | |

The filling occurs with 92% active substance solution and 8% propane/butane. The foam produces a good, flexible fixing and may be removed again by brushing out, without loading the hair.

Example 4

Foam-fixing Composition

| | |
|---|---|
| 1.00 g | polyvinylpyrrolidone |
| 1.00 g | PVP/vinyl acetate copolymer |
| 1.00 g | chitosan |
| 0.24 g | formic acid, 85% |
| 0.24 g | perfluorobutyric acid |
| 0.20 g | cetyltrimethyl ammonium chloride |
| 1.00 g | polyquaternium 16 |
| 10.00 g | ethanol |
| 85.32 g | water |
| 100.00 g | |

The filling occurs with 92% active substance solution and 8% propane/butane. The foam produces a good, flexible fixing and may be removed again by brushing out, without loading the hair. cl Example 5

Foam-fixing Composition With Strong Fixing Action

| | |
|---|---|
| 0.50 g | polyvinylpyrrolidone |
| 0.50 g | PVP/vinyl acetate copolymer |
| 0.50 g | high molecular weight, chitosan, 300,000 to 700,000 g/mol |
| 0.35 g | pyrrolidone carboxylic acid |
| 0.15 g | perfluorobutyric acid |
| 0.20 g | cetyltrimethyl ammonium chloride |
| 1.00 g | polyquaternium 16 |
| 10.00 g | ethanol |
| 86.80 g | water |
| 100.00 g | |

The filling occurs with 92% active substance solution and 8% propane/butane. The foam produces a good, flexible fixing and may be removed again by brushing out, without loading the hair.

Example 6

Foam-fixing Composition Without Ethanol

| | |
|---|---|
| 1.00 g | polyvinylpyrrolidone |
| 1.00 g | PVP/vinyl acetate copolymer |
| 1.00 g | chitosan |
| 0.24 g | formic acid, 85% |
| 0.29 g | perfluoropentanoic acid |
| 0.20 g | cetyltrimethyl ammonium chloride |
| 1.00 g | polyquaternium 16 |
| 95.27 g | water |
| 100.00 g | |

The filling occurs with 92% active substance solution and 8% propane/butane. The foam produces a good, flexible fixing and may be removed again by brushing out, without loading the hair.

Example 7

Foam-fixing Composition Providing Increased Luster

| | |
|---|---|
| 1.00 g | polyvinylpyrrolidone |
| 1.00 g | PVP/vinyl acetate copolymer |
| 1.00 g | chitosan |
| 0.24 g | formic acid, 85% |
| 0.29 g | perfluorocaprylic acid |
| 0.20 g | cetyltrimethyl ammonium chloride |
| 1.00 g | polyquaternium 16 |
| 0.10 g | ethoxylated fatty alcohol |
| 0.20 g | polydimethylsiloxane |
| 20.00 g | ethanol |
| 74.97 g | water |
| 100.00 g | |

The filling occurs with 92% active substance solution and 8% propane/butane.

Example 8

Liquid Fixing Composition

| | |
|---|---|
| 1.00 g | vinyl acetate/crotonic acid copolymer, 60% solution in isopropanol/water (ARISTOFLEX ®) |
| 0.70 g | amphomer |
| 0.15 g | aminomethylpropanol |
| 0.20 g | mixture of perfluorinated phosphinic and phosphonic acids (Fluowet ® PL 80) |
| 0.10 g | glycerol |
| 50.00 g | ethanol |
| 0.50 g | perfume oil |
| 47.35 g | water |
| 100.00 g | |

The Amphomer and Aristoflex are dissolved in ethanol. Then aminomethylpropanol is added and stirred for 1 hour at room temperature. Subsequently the above-described remaining ingredients are added and finally the water.

Example 9

Gel-forming Fixing Composition

| | |
|---|---|
| 1.00 g | chitosan |
| 0.15 g | formic acid, 85% |
| 0.45 g | pentafluoropropionic acid |
| 3.00 g | vinylpyrrolidone/vinyl acetate copolymer |
| 1.00 g | hydroxyethylcellulose |
| 0.10 g | glycerol |
| 94.30 g | water |
| 100.00 g | |

Example 10

Gel-forming Fixing Composition With Strong Fixing Action

| | |
|---|---|
| 1.00 g | high molecular weight chitosan (MW = 300,000 to 700,000 g/mol) |
| 0.70 g | pyrrolidone carboxylic acid |
| 0.35 g | perfluoropentanoic acid |
| 3.00 g | vinylpyrrolidone/vinyl acetate copolymer |
| 1.00 g | hydroxyethylcellulose |
| 0.10 g | propylene glycol |
| 30.00 g | ethanol |
| 63.86 g | water |
| 100.00 g | |

Example 11

Gel-forming Fixing Composition With Strong Fixing Action

| | |
|---|---|
| 1.00 g | high molecular weight chitosan (MW = 300,000 to 700,000 g/mol) |
| 0.44 g | pyrrolidone carboxylic acid |
| 0.53 g | perfluoropropionic acid |
| 3.00 g | vinylpyrrolidone/vinyl acetate copolymer |
| 1.00 g | hydroxyethylcellulose |
| 0.10 g | propylene glycol |
| 30.00 g | ethanol |
| 63.86 g | water |
| 100.00 g | |

Example 12

Non-Aerosol Hair Spray

| | |
|---|---|
| 0.10 g | perfluorooctanoic acid |
| 0.40 g | aminomethylpropanol |
| 1.00 g | amphomer |
| 3.00 g | vinylpyrrolidone/vinyl acetate copolymer |
| 50.00 g | ethanol |
| 45.60 g | water |
| 100.00 g | |

The Amphomer and Aristoflex are dissolved in ethanol. Subsequently Fluorad® FX-1001 and then the vinylpyrrolidone/vinyl acetate copolymer is added and dissolved. Finally the water is added.

Example 13

Aerosol Hair Spray

| | |
|---|---|
| 0.10 g | perfluorooctanoic acid |
| 0.40 g | aminomethylpropanol |
| 2.00 g | amphomer |
| 3.00 g | vinylpyrrolidone/vinyl acetate copolymer |
| 50.00 g | ethanol |
| 44.70 g | water |

-continued

| | |
|---|---|
| 100.00 g | |

The aminomethylpropanol is provided in the ethanol and the amphomer is dissolved in that solution. The remaining ingredients are added and dissolved. Subsequently it is filled together with propane/butane.

Example 14

Hair Fixing Composition

| | |
|---|---|
| 1.00 g | chitosan |
| 0.24 g | formic acid, 85% |
| 0.29 g | perfluoropentanoic acid |
| 10.00 g | ethanol |
| 88.47 g | water |
| 100.00 g | |

Example 15

Sprays with reduced VOC Content

Attempts were made to prepare VOC-55 sprays and VOC-80 sprays with a chitosan content according to the acids used for neutralization of the chitosans.

| VOC-55 Formulation: | |
|---|---|
| Chitosan | 4.0 g |
| Neutralizing Agent (see Table I) | the amount required for complete neutralization of chitosan |
| Ethanol | 20 g |
| Dimethyl ether | 35 g |
| Water | to 100 g |

| VOC-80 Formulation: | |
|---|---|
| Chitosan | 4.0 g |
| Neutralizing Agent(see Table 1) | the amount required for complete neutralization of chitosan |
| Ethanol | 40 g |
| Dimethyl ether | 35 g |
| Water | to 100 g |

The results are shown in the following Table I.

TABLE I

RESULTS OF ATTEMPTS TO MAKE VOC SPRAYS

| NEUTRALIZING AGENT | RESULTS FOR VOC 80 FORMULATION | RESULTS FOR VOC 55 FORMULATION |
|---|---|---|
| Formic Acid | Precipitation of Chitosan | Precipitation of Chitosan |
| Pyrrolidone-Carboxylic acid | Precipitation of Chitosan | Two-phased, rapid Precipitation |
| Lactic Acid | Precipitation of Chitosan | Two-phased, rapid Precipitation |
| 3,6,9-trioxaun-decanoic acid | Precipitation of Chitosan | Precipitation of Chitosan |
| Perfluoropentanoic Acid | Single phase, clear | Single phase, clear |

A single phase, low viscosity formulation sprayable without preliminary shaking is produced only using the fluorinated acid, perfluoropentanoic acid.

The disclosure in German Patent Application 198 05 434.3-41 of Nov. 2, 1998 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair treatment compositions containing fluorinated acids and polymers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A hair treatment composition containing a complex formed from at least one fluorinated acid and chitosan.

2. The hair treatment composition as defined in claim 1, containing from 0.01 to 10 percent by weight of said at least one fluorinated acid or said fluorinated acid salt.

3. The hair treatment composition as defined in claim 1, wherein said at least one fluorinated acid has the formula (I)

$$A\text{---}(CH_2)_x\text{---}(CF_2)_y\text{---}(CH_2)_z\text{---}B \qquad (I),$$

in which x and z, independently of each other, are each a number from 0 to 5, y is a number from 1 to 21, A is an acid group and B is either a fluorine atom or an acid group, with the proviso that said z has the value 0 when B represents said fluorine atom.

4. The hair treatment composition as defined in claim 3, wherein said A and B are each, independently of each other, selected from the group consisting of —COOH, —SO$_3$H, —OPO$_3$H$_2$ and —OPO$_2$H.

5. The hair treatment composition as defined in claim 1, containing from 0.01 to 20 percent by weight of said chitosan.

6. A hair treatment composition containing
   a complex formed from at least one fluorinated acid and chitosan, and
   at least one film-forming, hair-fixing polymer.

7. The hair treatment composition as defined in claim 6, containing from 0.01 to 10 percent by weight of said at least one fluorinated acid or said fluorinated acid salt.

8. The hair treatment composition as defined in claim 6, wherein said at least one fluorinated acid has the formula (I)

$$A\text{---}(CH_2)_x\text{---}(CF_2)_y\text{---}(CH_2)_z\text{---}B \qquad (I),$$

in which x and z, independently of each other, are each a number from 0 to 5, y is a number from 1 to 21, A is an acid group and B is either a fluorine atom or an acid group, with the proviso that z has the value 0 when B represents said fluorine atom.

9. The hair treatment composition as defined in claim 8, wherein said A and B are each independently selected from the group consisting of —COOH, —SO$_3$H, —OPO$_3$H$_2$ and —OPO$_2$H.

10. The hair treatment composition as defined in claim 6, containing from 0.01 to 20 percent by weight of said chitosan.

11. The hair treatment composition as defined in claim 6, wherein said basic groups of said at least one polymer are from 5 to 70 percent neutralized with said at least one fluorinated acid.

12. The hair treatment composition as defined in claim 11, wherein said basic groups, which are not neutralized with said at least one fluorinated acid, are neutralized with at least one additional non-fluorinated acid.

13. The hair treatment composition as defined in claim 6, containing from 0.01 to 50 percent by weight of said at least one film-forming, hair-fixing polymer.

14. An aerosol spray comprising chitosan or a basic chitosan derivative compound, at least one fluorinated acid, water, and at least one propellant, and containing no more than 80 percent by weight of volatile organic compounds.

* * * * *